US 6,602,240 B2

(12) United States Patent
Hermann et al.

(10) Patent No.: US 6,602,240 B2
(45) Date of Patent: Aug. 5, 2003

(54) METHOD AND DEVICE FOR MAINTAINING A SEAL

(75) Inventors: George D. Hermann, Portola Valley, CA (US); Bradley Hill, Woodside, CA (US); Thomas Howell, Palo Alto, CA (US); David Willis, Palo Alto, CA (US); Neil Holmgren, Alameda, CA (US); Joshua Whittemore, Portola Valley, CA (US)

(73) Assignee: Thomas J. Fogarty, Portola Valley, CA (US)

(*) Notice: Subject to any disclaimer, the term of this patent is extended or adjusted under 35 U.S.C. 154(b) by 0 days.

(21) Appl. No.: 09/784,871

(22) Filed: Feb. 15, 2001

(65) Prior Publication Data
US 2002/0007152 A1 Jan. 17, 2002

Related U.S. Application Data
(60) Provisional application No. 60/182,640, filed on Feb. 15, 2000.

(51) Int. Cl.[7] ............................................. A61M 31/00
(52) U.S. Cl. .................. 604/500; 604/34; 604/167.06; 604/164.07; 604/165.02; 604/171; 251/4
(58) Field of Search .................. 604/34, 171, 250, 604/164.07, 165.01, 165.02, 167.06, 500; 251/4, 145, 146; 137/355.18; 138/43, 45, 46

(56) References Cited

U.S. PATENT DOCUMENTS

| | | | | |
|---|---|---|---|---|
| 2,902,248 A | * | 9/1959 | Barton et al. | 137/613 |
| 3,613,661 A | * | 10/1971 | Shah | 128/831 |
| 4,378,013 A | * | 3/1983 | LeFevre | 251/7 |
| 4,436,519 A | | 3/1984 | O'Neill | |
| 4,575,041 A | * | 3/1986 | Hu | 251/4 |
| 4,702,733 A | * | 10/1987 | Wright et al. | 604/250 |
| 4,738,658 A | | 4/1988 | Magro et al. | |
| 5,125,911 A | * | 6/1992 | Grabenkort et al. | 128/912 |
| 5,376,077 A | * | 12/1994 | Gomringer | 604/167.06 |
| 5,401,256 A | * | 3/1995 | Stone et al. | 251/10 |
| 5,423,762 A | | 6/1995 | Hillstead | |
| 5,429,616 A | * | 7/1995 | Schaffer | 604/167.06 |
| 5,685,858 A | | 11/1997 | Kawand | |
| 5,865,721 A | * | 2/1999 | Andrews et al. | 600/18 |
| 6,113,062 A | * | 9/2000 | Schnell et al. | 251/10 |
| 6,346,093 B1 | * | 2/2002 | Allman et al. | 604/164.03 |

* cited by examiner

Primary Examiner—Brian L. Casler
Assistant Examiner—Jeremy Thissell
(74) Attorney, Agent, or Firm—Morrison & Foerster LLP

(57) ABSTRACT

According to the present invention, improved methods and apparatus are provided for regaining hemostasis or otherwise minimizing leakage during endoluminal, surgical or percutaneous intraluminal procedures, and for providing a seal during laparoscopic surgical procedures where there is leakage of the $CO_2$ insufflation, when the primary means of hemostasis or pneumatic $CO_2$ seal is compromised or fails. More particularly the present invention relates to devices having a front hub and a rear hub, one or other of which is adapted to retain a compression seal such that when the front and rear hub are matingly engaged, axial and radial pressure is applied to the compression plug and any devices located therebetween, thereby achieving a seal. The compression device can be applied while a guidewire or additional devices remain within the leaking sheath or trocar, thereby allowing the physician to maintain hemostasis or adequate $CO_2$ insufflation, without exchanging the introducer sheath or laparoscopic port.

16 Claims, 11 Drawing Sheets

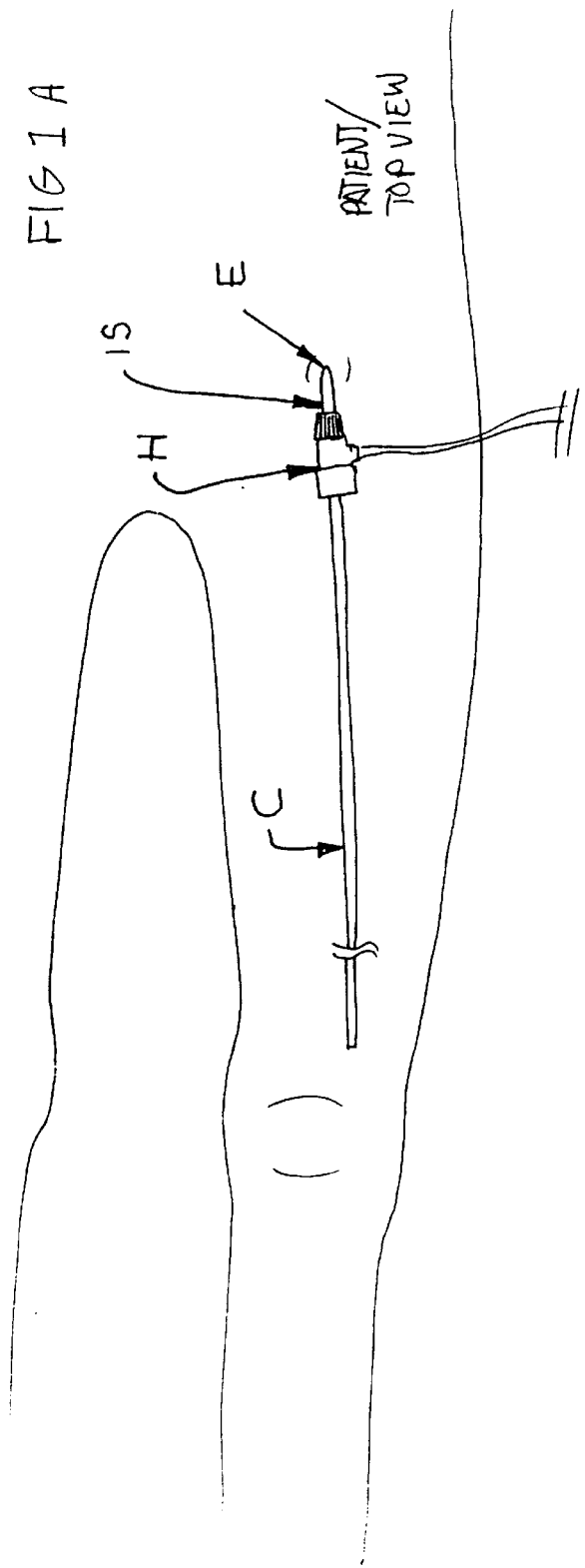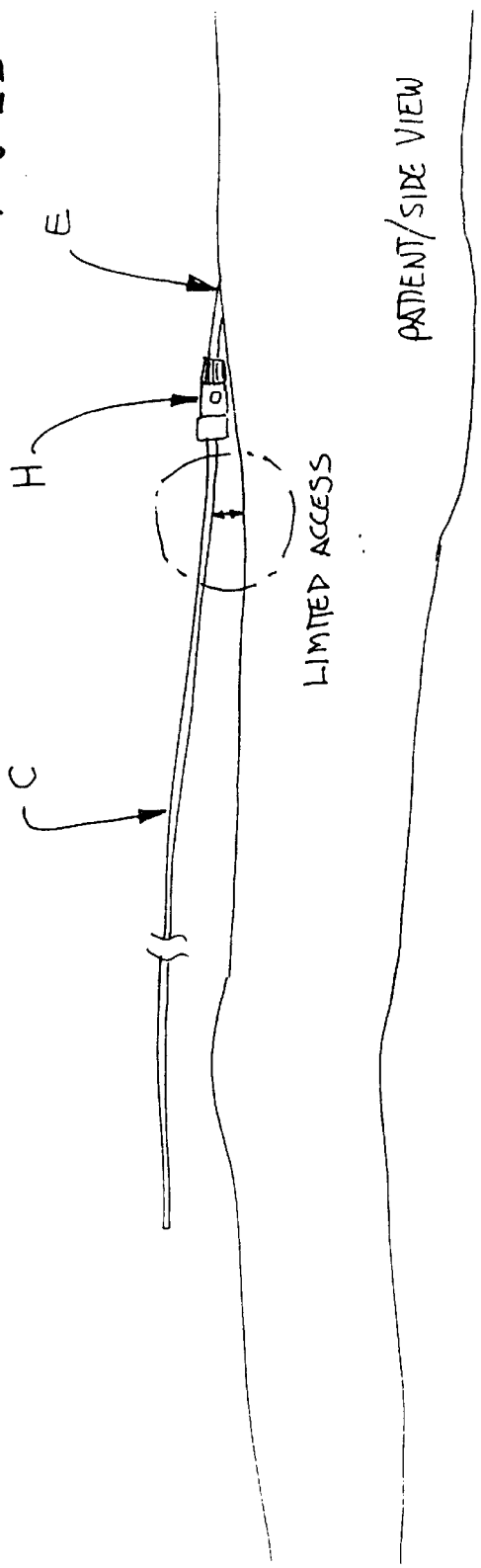

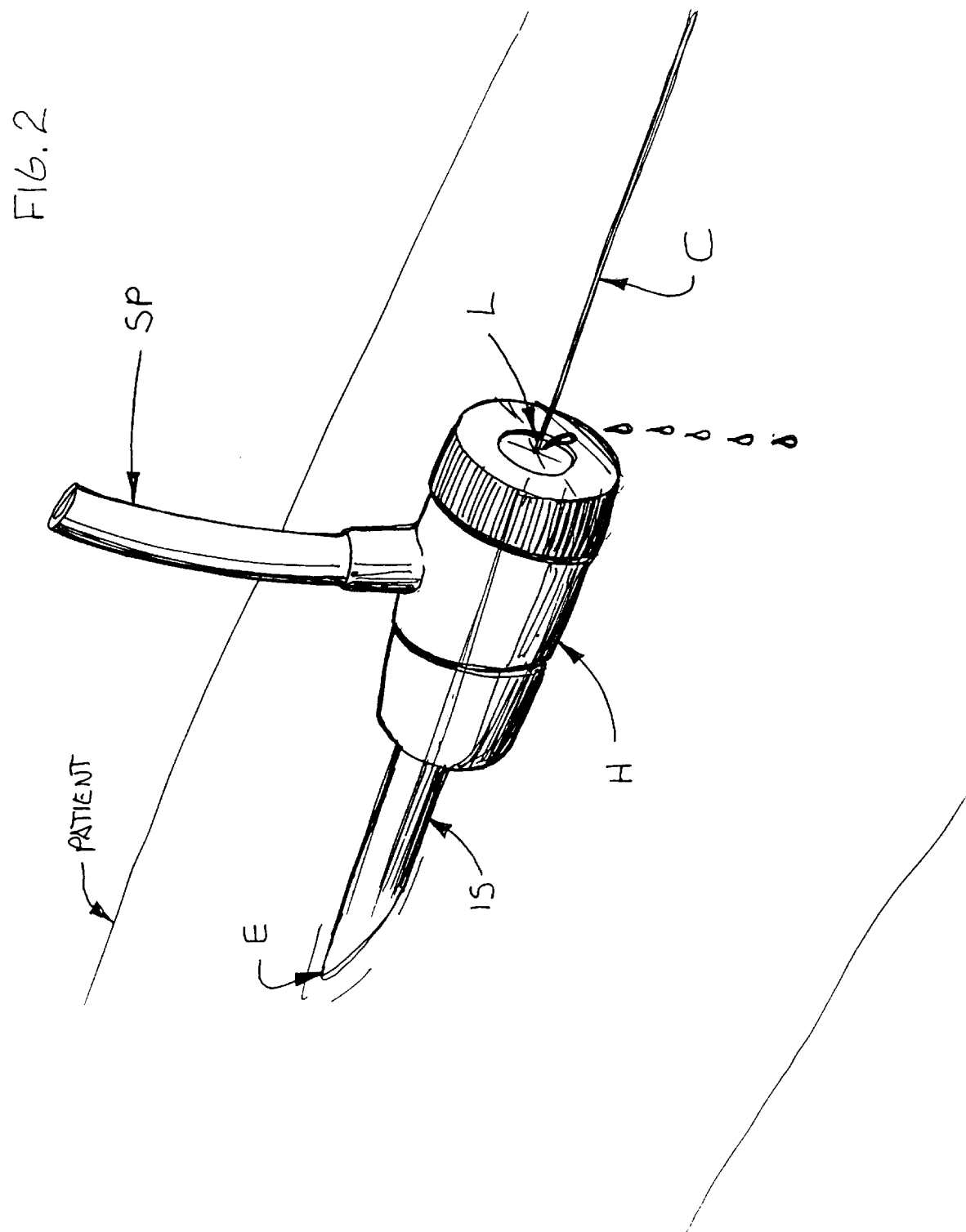

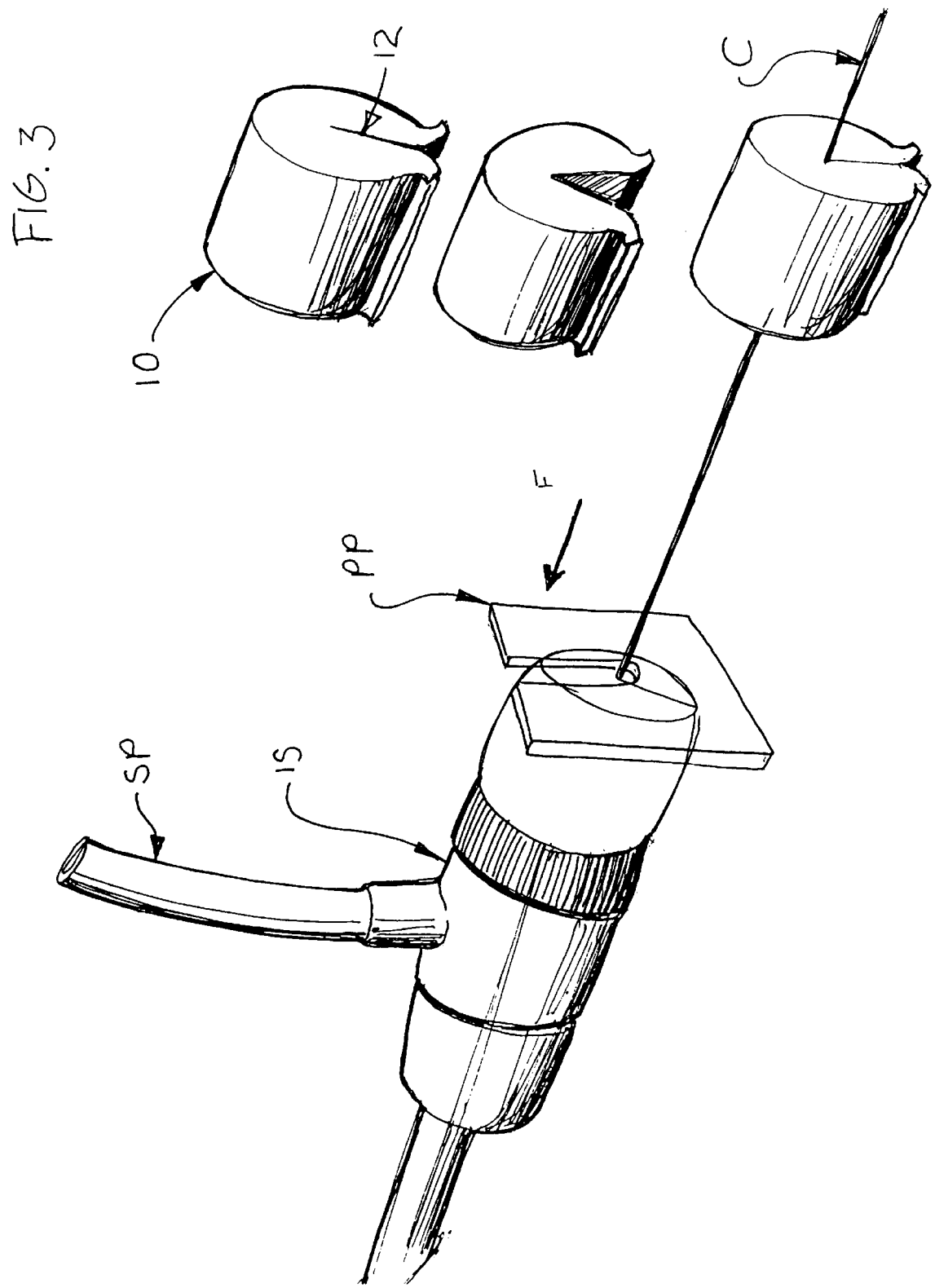

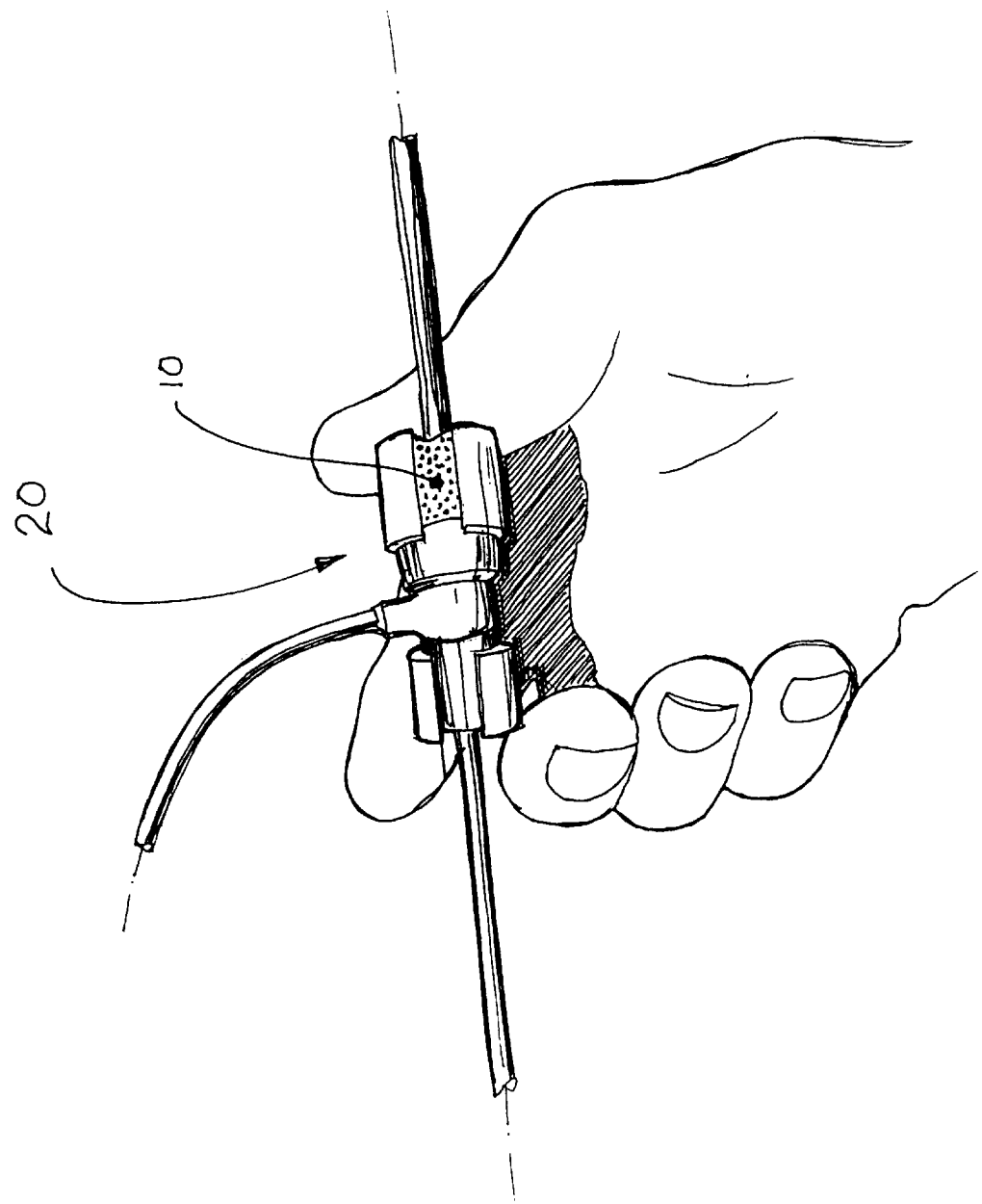

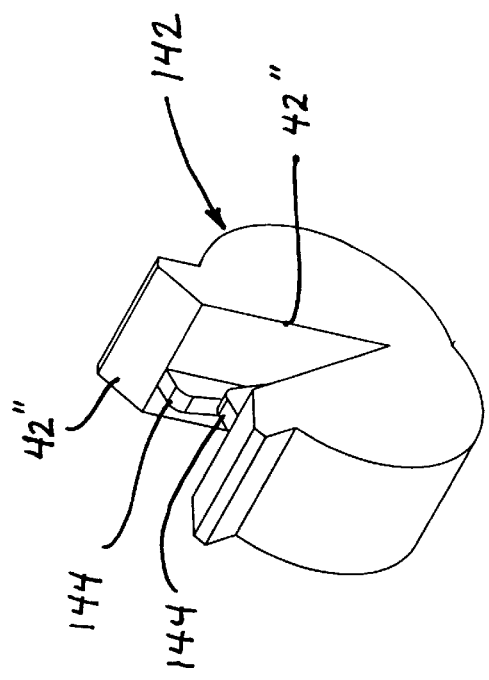
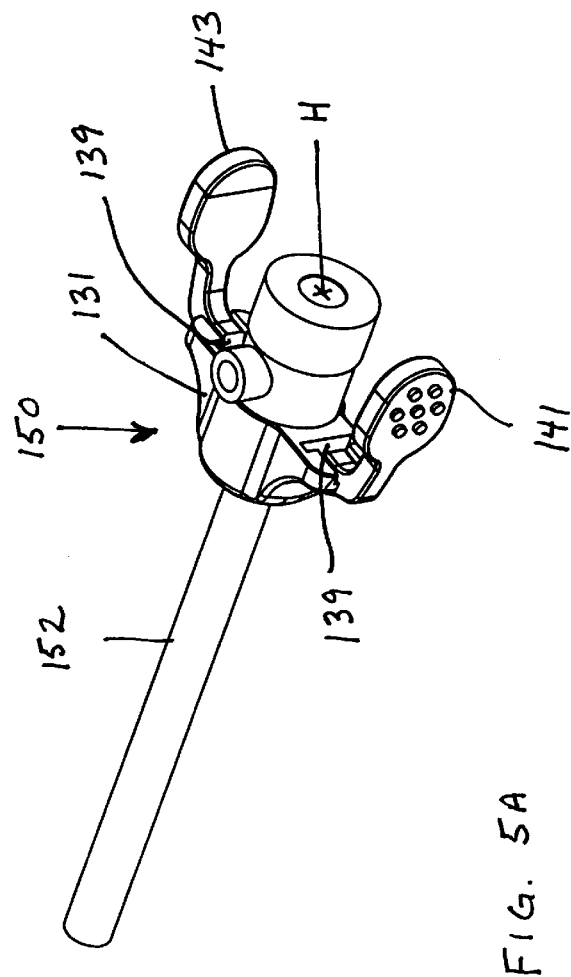
FIG. 5B
FIG. 5A

METHOD AND DEVICE FOR MAINTAINING A SEAL

This application claims benefit of priority under 35 U.S.C. §119(e) of U.S. Provisional Application No. 60/182,640, filed Feb. 15, 2000, and which is incorporated herein in its entirety.

BACKGROUND OF THE INVENTION

The present invention relates generally to medical devices and methods and more particularly to devices and methods for sealing the lumen of a medical device for maintaining hemostasis (control of bleeding) attendant to the use of minimally invasive transluminal, endoluminal and other such devices and procedures wherein devices such as sheaths, through which other catheter devices are passed, are inserted percutaneously or surgically into a blood vessel of a patient, or in cases of laparoscopic procedures where sealing the lumen is to control the leakage of $CO_2$ gas used to insufflate a body cavity.

Minimally invasive interventions have become increasingly popular for approaching a variety of diseases such as the diagnosis and treatment of coronary heart disease using stent devises, laparoscopic procedures in general surgery, neurovascular disease for implanting coils, stents and other procedures, venous disease for placing vena cava filters or other procedures, as well as treatment of abdominal aortic aneurysms using stent grafts that are placed in the aorta or other vessels. The sizes of the catheter devices used to perform these therapies can range from 3 French to 30 French (0.039" to 0.393"). Typically the devices that are used are within a 7 to 24 French (0.066" to 0.315") diameter.

In procedures such as these, a device known as an access sheath, also known as an introducer sheath, is typically placed through the skin in the upper thigh area of a patient's leg, either through a surgical cutdown or a percutaneous puncture, and down into the lumen of a blood vessel (vein or artery) with a technique known as the Seldinger technique (physician uses the "flashback" or blood spurt to confirm that the center of the lumen has been reached by the device), once a sheath is placed, most procedures employ catheter devices that are then inserted through the sheath and into the blood vessel at some distance away from the intended treatment site, and are then advanced through the vessel lumen until the selected treatment location is reached. In most instances this approach is performed "over the wire", a technique that requires the physician to first place a guidewire device through the sheath and into the vessel lumen over which the larger catheter device can be tracked to the remote location.

The access sheaths that are employed for initial entry into the vessel typically include an integral hemostasis valve of some kind on the proximal portion of the device. There are numerous designs, including "duck-bill" type valves, valves that stretch and re-coil to accommodate various devices such as "iris" type valves, and various perforated elastomer valves. For example, U.S. Pat. No. 4,436,519 discloses a removable hemostasis valve having a "duck bill" type construction. U.S. Pat. No. 5,685,858 discloses a sliding valve for use with a catheter when no sheath is used. U.S. Pat. No. 4,738,658 discloses a tapered valve for use when a sheath is removed. U.S. Pat. No. 5,423,762 discloses a modular catheter sheath introducer with a replaceable hemostasis valve. During a procedure, however, these valves can fail, leading to leakage around the catheter and the valve, resulting in increased blood loss.

Given the popularity of less invasive techniques and their success, a broad range of devices or varying diameters are being used through sheaths, and the procedures are becoming increasingly complex and time consuming, making hemostasis over the duration of the procedure of paramount importance. A common problem during these procedures is a "leaky valve", or the inability to maintain hemostasis around the catheter or wire using the integral sheath valve. In many procedures using larger devices such as aortic stent grafting, leaking valves can be quite commonplace. Currently, some surgeons and interventionists (radiologists, cardiologists) resort to tying gauze strips around the leaking section in an attempt to stem the flow of leaking blood. Typically the gauze just absorbs the blood and does not provide a durable solution. Various attempts have been made to come up with an improved integrated valve to deal with these issues with limited success.

There is a need for improved ancillary devices and methods for more effectively maintaining hemostasis, often after the existing valves have degenerated during a procedure, either due to multiple catheter exchanges (a time during the procedure when no catheter is in place and only a guidewire remains in the sheath), or the use of large catheter devices such as during the placement of stent grafts (some up to 32 French). It would be desirable to have an ancillary device that allows a physician to quickly regain hemostasis during the procedure thereby minimizing blood loss, while still being able to pass additional devices through the indwelling sheath once the ancillary device is placed, and complete the procedure as intended.

It would be desirable to have a device that can be applied to an existing sheath device to provide axial compression along the shaft of the sheath device and radial pressure around any devices introduced through the sheath, to block any leakage that may be flowing from the compromised valve at the proximal end of the sheath. Such a device would need to accommodate a guidewire and other catheters to pass through it so that the procedure can be completed. In addition, it would be desirable for such a compression device to be fixedly connected to said sheath during the time when hemostasis is desired, but also be removable from the sheath device in the event that the sheath is removed or changed during the procedure, or is no longer necessary.

Furthermore, it would be desirable to have a system of devices and methods that are easily applied around an indwelling sheath, either by the physician or the assisting staff, and that do not add unacceptable bulk to the catheter body already in place against the patient's skin. It is desirable that such improved devices be cost effective and adaptable to accommodate various sheath sizes, while still allowing the physician to pass additional catheters and instruments through the ancillary devices while continuing to minimize blood loss.

It would be further desirable to apply the compression device of the present invention to achieve hemostasis without requiring the removal of any indwelling instrumentation (such as catheters and guidewires), or having to thread such compression device over the entire length of the indwelling instrumentation to reach the desired point of hemostasis.

SUMMARY OF THE INVENTION

These and further objectives and advantages are met by the design and use of the various embodiments of the present invention. The present invention provides for improved methods and apparatus for providing a seal around a primary treatment device, such as, for example, regaining hemostasis during an intraluminal procedure when the primary means of hemostasis is compromised or fails, or in the case of laproscopic procedures, to control leakage of gas used to insufflate a body cavity. For purposes of this specification, the terms "standard introducer sheath" or "catheter", or "integral valve", "laparoscopic trocar or port" or "guidewire" shall all refer to primary treatment devices that have been placed in the patient prior to a medical procedure or during the procedure, usually endoluminally or percutaneously. Usually a standard introducer sheath will have an integral valve or elastic orifice at the proximal end to aid in hemostasis, but still allow the passage of therapeutic or diagnostic devices therethrough. In some instances, a sheath is not used, and therefore the therapeutic device may be a primary treatment device itself, such as a catheter with a valve. It should be noted however, that in the case of a procedure performed without a sheath the device of the present invention may be applied as the primary means of sealing by way of attachment around the proximal portion of the treatment device, such as a laparoscopic trocar or an endoluminal stent graft delivery device.

To achieve such sealing, the invention provides for a compressible, resilient plug that is adapted for positioning at the proximal end of a sheath device, i.e., an introducer sheath or other primary treatment device described above. The plug includes a slit extending longitudinally of the plug and opening to an outer surface of the plug in order to receive a therapeutic or diagnostic device, such as a catheter, guidewire, trocar, etc., that is operationally passed through the sheath device. The invention further provides means for compressing the plug, thereby providing axial pressure against the sheath device as well as radial inward pressure against the therapeutic or diagnostic device to maintain a seal and minimize leakage from the sheath device.

In particular, in a first embodiment of the present invention a compression device is provided having a rear hub and a front hub adapted to be placed around the shaft of a standard introducer sheath proximal end. The front hub and rear hub are operatively connected to two or more ratchet projections extending from one or other of the hubs, and adapted to be engaged into slots housed on the other hub. The compression device is preferably formed in a substantially cylindrical configuration having a longitudinal opening at some point around the circumference of the device for receiving the shaft of a standard catheter device from a sideloading position. The front hub preferably has at least two receiving slots formed in the sidewall thereof and defined further by release tab members extending therefrom. The rear hub includes two or more longitudinal projecting elements adapted for mating engagement with the front hub receiving slots. The rear hub further comprises a housing to receive a compression plug valve of the present invention.

In an alternate embodiment of the present invention, the compression device has a single ratchet mechanism. The combination of the front and rear hub is achieved by interlocking a ratcheting member shaft adapted to extend longitudinally from the front hub, and a corresponding ratchet member shaft extending longitudinally from the rear hub, said rear hub further having a through hole at the base of the rear hub, to receive the shaft of the front hub ratchet member.

In a further alternate embodiment of the present invention, the front and rear hub matingly engage upon insertion of the front hub into the cylinder of the rear hub (or vice versa), each hub including a threaded surface on either the inside or outside of the cylinder of the hub, depending on which one is to be inserted into the other.

In a further alternate embodiment, the compression device of the present embodiment is configured in the arrangement of a side-loading clamp, having a front portion and a rear portion and adapted to fit over the proximal end of a standard sheath and integral hemostasis device. This embodiment includes a front clamp to stabilize the compression device around the shaft of the standard introducer sheath or catheter, and an independently operating rear clamp having a housing for a compression plug, once the rear clamp is placed around the proximal portion of the introducer sheath and up against the integral valve, the compression plug operates to seal off any leakage.

In an exemplary use of the present invention, upon noticing that the hemostasis valve of the standard sheath (inserted in the patient) has begun to leak, a physician or assisting staff member will take the compression device of the present invention and place the introducer sheath catheter shaft and the proximal portion of the introducer sheath (usually valve end) into the longitudinal openings of the front and rear hub of the present invention, respectively (e.g. side loading the catheter shaft into the compression device). The operator will then operate the compression device of the present invention to engage the front and rear hub, bringing the compression pad of the present invention into contact with the leaking end of the introducer sheath, thereby applying axial pressure along the shaft of the introducer sheath and compressing radially around any device inserted therethrough, and abating any fluid flow from the sheath valve. The rear hub and compression device are adapted to receive a guidewire and other devices and therefore, the medical procedure already in process may then resume through the existing introducer sheath and the compression device of the present invention.

BRIEF DESCRIPTION OF THE DRAWINGS

FIGS. 1A and 1B illustrate a top view and side view of a standard sheath and catheter system placed in the upper thigh of a patient to illustrate the relative placement of the sheath system to the leg of the patient.

FIG. 2 illustrates a standard percutaneous entry site into the leg of a patient with a generic sheath having an integral hemostasis valve on the proximal portion thereof. In addition a guidewire is shown through the lumen of the valve and the resultant leak.

FIG. 3 illustrates a schematic assembly of the present invention depicting the application of axial pressure against the proximal face of the generic hemostasis valve using a pressure plate and compression plug of the present invention.

FIG. 4 is a schematic representation of the device of the present invention in use over a standard introducer sheath device proximal end.

FIG. 5A illustrates another embodiment of the present invention where the front hub portion of FIG. 5 is integral to an introducer sheath.

FIG. 5B illustrates a modified version of the compression plug of FIG. 3.

DETAILED DESCRIPTION OF THE INVENTION

FIGS. 1A and 1B are provided to illustrate the standard placement of an introducer sheath or endovascular or interventional catheter through a "groin incision" or puncture in the upper thigh of a patient. FIG. 1B illustrates a top view of an entry site (E), through which an introducer sheath (IS) has been placed, the introducer sheath IS including an integral hemostasis mechanism (H) and a through element such as a catheter or guidewire (C) extending therethrough. FIG. 1A illustrates a side view of the same standard placement of introducer sheath (IS) and catheter (C) with integral hemostasis sheath to show the angle of the catheter relative to the patient's limb. As seen, due to the limited access space between the patient's limb and the catheter C, it is desirable that the device of the present invention be of a low profile construction for integration with the existing sheath.

In the case of the placement of the IS through the entry site (E) of a patient as illustrated in FIG. 2, the integral hemostasis sheath may deform or otherwise become incompetent such that hemostasis is compromised and leakage (L) of blood results. This can be caused by multiple "exchanges" or insertions of various catheter devices of varying diameters (guidewires, therapeutic devices such as angioplasty balloons, stents, or stent grafts, or other such treatments) through the indwelling sheath during the course of a treatment. Typically such a standard introducer sheath (IS) includes a side port (SP) integral thereto that can connect the sheath to infusion, suction, or other functions.

FIG. 3 illustrates a schematic representation of the function of the present invention that operates to apply axial and/or radial compression to the introducer sheath (IS) at the point of the leak, that usually occurs at the rear portion of hemostasis sheath where devices are exchanged. In this schematic, the compression plug 10 is adapted to be applied, or "side-loaded", over the wire by way of an axial slit 12 projecting from the central axis of the center of the compression plug 10. In conjunction with the device of the present invention (shown in later figures), the compression plug 10 applies compression as represented schematically by pressure plate (PP) in this figure, when a force (F) is applied.

In operation, as illustrated in FIG. 4, the compression device of the present invention 20 is loaded from the side of the standard introducer sheath (IS) to accommodate the placement of the compression device against the thigh of the patient, and to accommodate the side port (SP) if present, and any therapeutic devices already residing in the sheath. As this Figure illustrates, the compression device 20 of the present invention, including compression plug 10, is manipulated with a single hand of the operator and configured to extend on either side of the introducer sheath (IS) for ease of placement.

Figure 5:
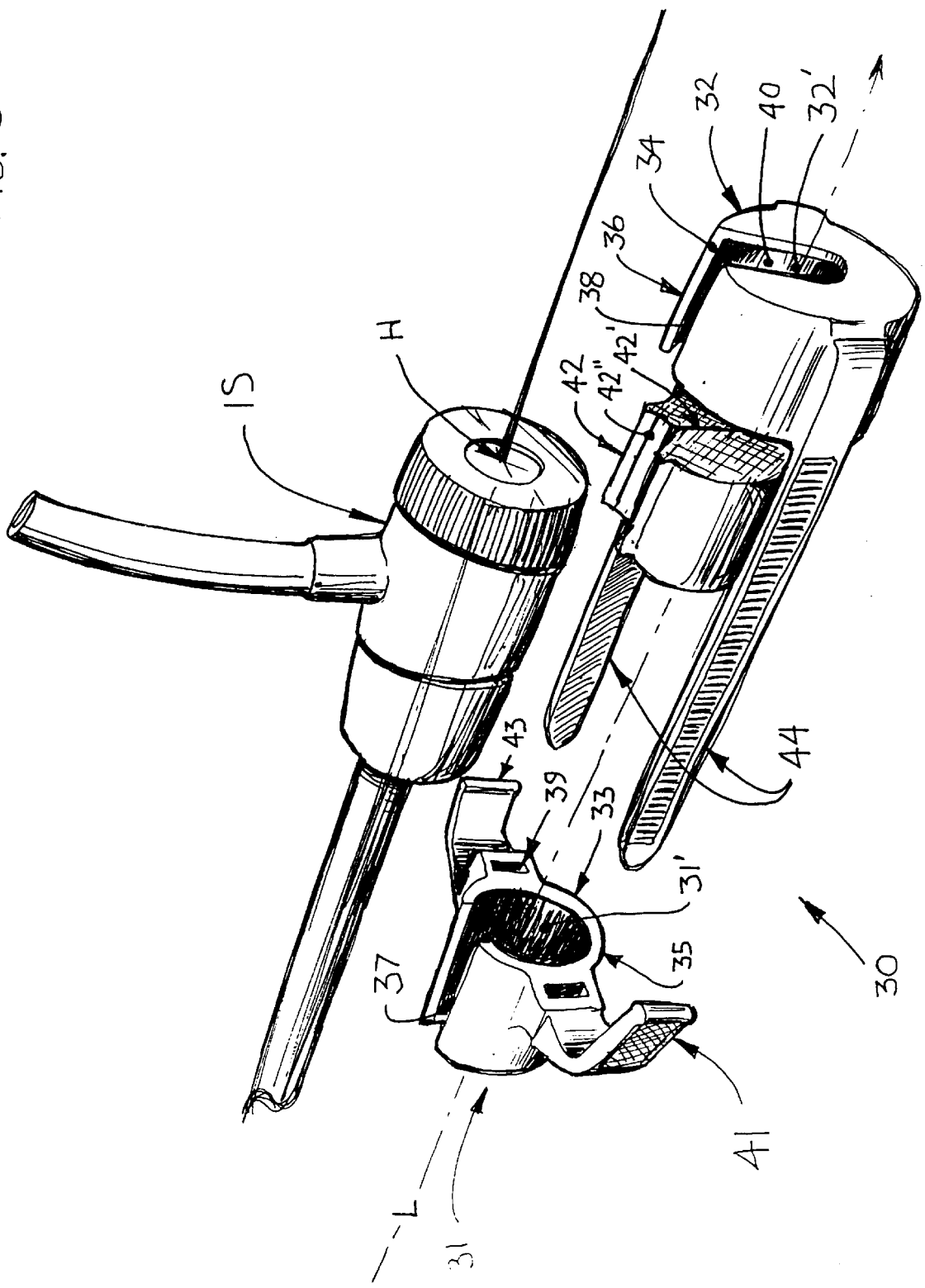
FIG. 5 illustrates a first embodiment of the present invention having a front hub and a rear hub connected to longitudinal ratchet projections that run on opposing sides of the rear hub such that when connected the device of the present invention may be placed around the proximal portion of standard introducer sheath. The rear hub further including housing for purposes of receiving a compression plug of the present invention.

An exemplary compression device constructed in accordance with a first embodiment of the present invention is illustrated in FIG. 5. The compression device 30 comprises a front hub 31 and a rear hub 32 adapted for operative engagement around the proximal portion of standard introducer sheath (IS). Front hub 31 is formed in a generally circumferential configuration having a lumen 31' therethrough and extending along a longitudinal axis (L), and further defining an inner periphery 33 and an outer periphery 35. Front hub 31 further includes a longitudinal opening 37 along the axis of front hub 31 allowing for placement of the hub body around the shaft of introducer sheath (IS). Front hub 31 further comprises one or more slots 39 formed within the inner periphery 33 and the outer periphery 35. Front hub 31 also includes release tabs 41 and 43 extending laterally from said front hub 31 and subsequently in a curvilinear direction along the longitudinal axis of said front hub 31.

Compression device 30 further comprises a rear hub 32 formed in a generally circumferential configuration having a lumen 32' therethrough and extending along a longitudinal axis (L), and further defining an inner periphery 34 and an outer periphery 36. Rear hub 32 further includes a longitudinal opening 38 along the axis of rear hub 32 allowing for placement of the rear hub body around the integral valve (H) of the introducer sheath (IS). Rear hub 32 includes a cavity 40 adapted to receive a compression plug 42 therein. Compression plug 42 is adapted to receive a guidewire or other catheter device by way of a slot 42' extending laterally from the center of the plug. In a preferred embodiment slot 42' includes a bevel 42" to act as a channel for receipt of the guidewire (C) or other catheter and thereby guide the catheter to the center of the plug and aid the ease of application of the compression device 30 to the sheath (IS). Preferably the slot 42' is aligned with the longitudinal opening 38 of the rear hub 32. Compression plug 42 can be formed from various materials such as urethane, rubber (RTV), foam (opened or closed cell) or other elastomer, preferably silicone. The preferable dimensions of the plug are in the range of the diameter of 0.5" to 1.5". As shown in FIG. 5B, compression plug 142 can further be provided with protrusions 144, 144 located within slot 42' and extending from the opposing slot faces. These protrusions are preferably formed of the same material as the plug itself, and operate to provide for increased sealing around the catheter when the plug is compressed during operation of the device, as further described.

Rear hub 32 further includes projection elements 44 extending from the outer periphery 36 along the longitudinal axis of the rear hub 32, and adapted to be received by the slots 39 of front hub 31. Projections 44 preferably have a serrated or ratchet surface on one or both sides to allow projections 44 to fixedly connect within the slots 39. The preferred dimensions of the cavity 40 are such that the cavity accommodates most commercially available sheaths.

In operation, compression plug 42 is seated in cavity 40 and projections 44 are initially engaged by the operator with slots 39 to form an integral device (front and rear hub) that can be "side loaded" over the body of introducer sheath (IS)

through longitudinal opening 37 of the front hub 31 and 38 of the rear hub and 32 of the compression plug 42. The operator can then place preferably his or her index finger and middle finger on release tabs 41 and 43 respectively, and thumb on the proximal end of rear hub 32 and further engage the front and rear hub until the compression plug 42 exerts sufficient axial compression against the proximal valve (H) of introducer sheath (IS) and any existing leakage is stopped. To release the compression device of the present invention, the operator may place lateral digital compression against the release tabs 41 and 43, thereby releasing the engagement of the ratcheting mechanisms of longitudinal projections 44 from slots 39. Front hub 31 and rear hub 32 can then be separated and disengaged from introducer sheath (IS). It is contemplated as part of the present invention that compression device 30, may be re-applied to the introducer sheath (IS) sometime later in a given procedure if necessary.

An alternate embodiment of the present invention is illustrated in FIG. 5A. In this embodiment, features of the front hub described above are incorporated directly into introducer sheath 150 itself. As shown, projection tabs 143 extend from sheath 150 and include slots 139 for receiving corresponding projection elements of rear hub 44. Sheath 150 can be assembled in a variety of ways, including integrally forming the sheath body, or otherwise assembling the sheath in ways known in the art. For example, that portion of the sheath containing the projection tabs and slots can be threaded onto the sheath body.

Front hub 31 is formed in a generally circumferential configuration having a lumen 31' therethrough and extending along a longitudinal axis (L), and further defining an inner periphery 33 and an outer periphery 35. Front hub 31 further includes a longitudinal opening 37 along the axis of front hub 31 allowing for placement of the hub body around the shaft of introducer sheath (IS). Front hub 31 further comprises one or more slots 39 formed within the inner periphery 33 and the outer periphery 35. Front hub 31 also includes release tabs 41 and 43 extending laterally from said front hub 31 and subsequently in a curvilinear direction along the longitudinal axis of said front hub 31.

Figure 6:
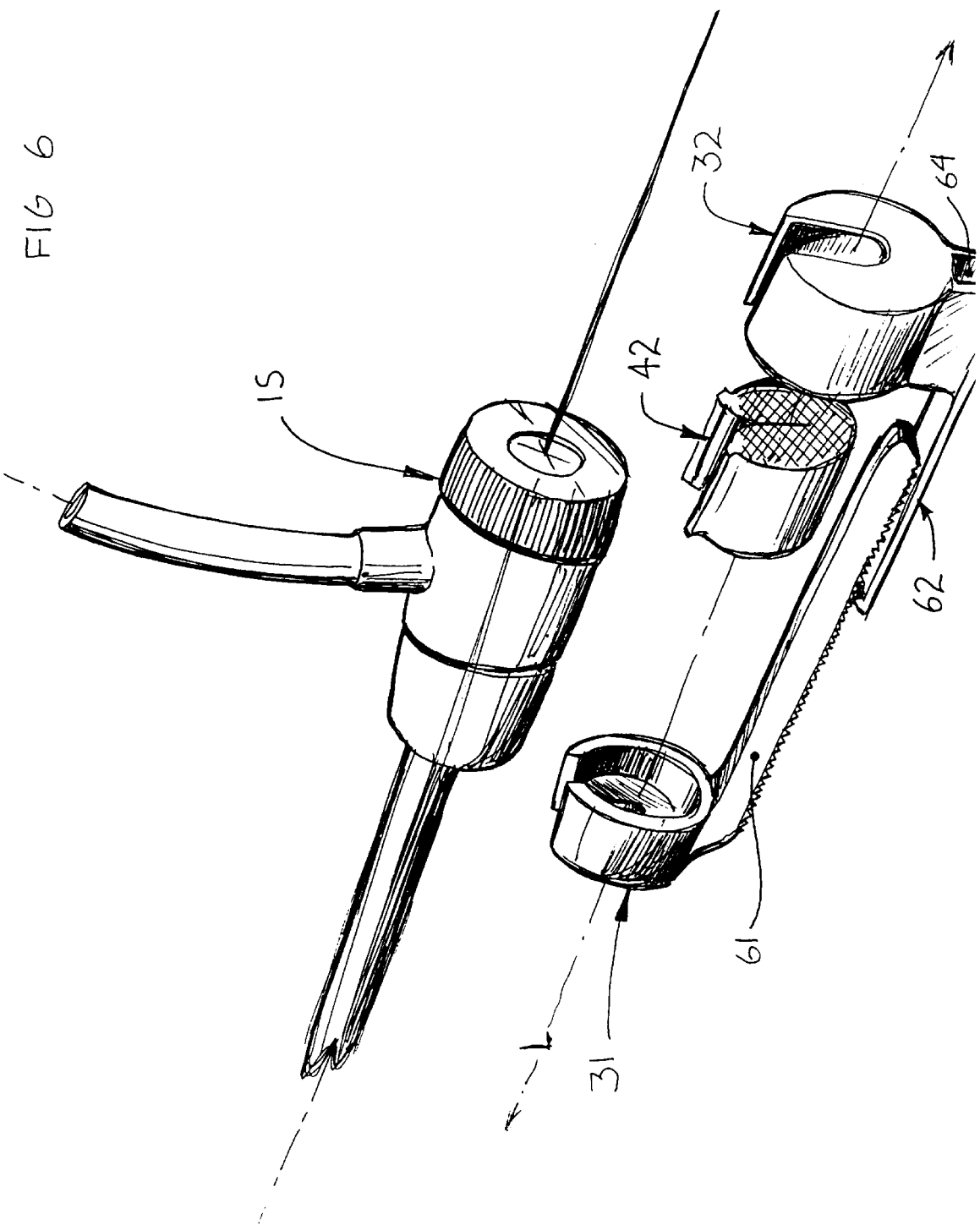
FIG. 6 illustrates a another embodiment of the present invention having a front hub and a rear hub connected to each other by a single ratchet projection on the front hub positioned to be received by the rear hub such that when connected, the device of the present invention may be placed around the proximal portion of a standard introducer sheath.

Another embodiment of the compression device of the present invention is illustrated in FIG. 6. In this embodiment, the compression device is provided with a single longitudinal front projection 61 extending from the front hub at a position at approximately 180° from the longitudinal slot 37 on front hub 31. The rear hub 32 in this secondary embodiment is formed in a similar fashion as earlier described, but having a single longitudinal rear projection 62 provided with ratchet type indentations adapted for an interdigitating fit with front projection 61. Rear hub 32 further includes a receiving slot 64 extending from the rear hub at a position at approximately 180° from the longitudinal slot 38 on front hub 31 for receipt of front projection 61. In this secondary embodiment, compression plug 42 is adapted to fit within the cavity 40 of the rear hub, as earlier described.

In operation, longitudinal front projection 61 is placed in contact with longitudinal rear project 62 and thereafter guided into receiving slot 64 to slidably engage front hub 31 and rear hub 32 thereby bringing compression plug 42 into contact with the proximal end of introducer sheath (IS) and any other matter therebetween.

Figure 7:
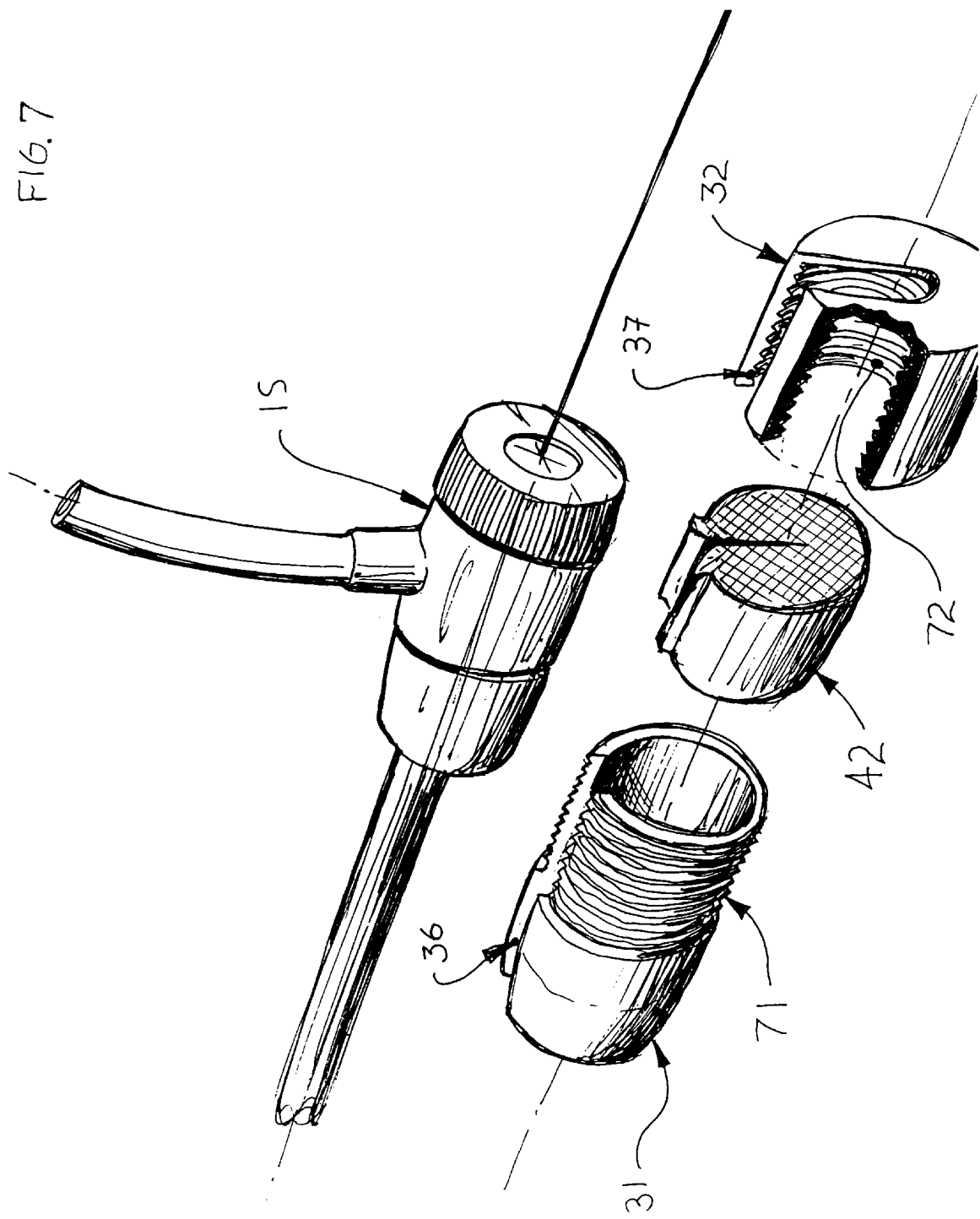
FIG. 7 illustrates a further alternative embodiment of the present invention having a front hub and a rear hub connected to each other by interlocking threads (internal and external) disposed on the shafts of said front and rear hubs.

In an alternative embodiment of the present invention as illustrated in FIG. 7, the front hub and rear hub have a similar circumferential configuration as previously described. In this embodiment however, each hub has an extension of the hub body around its circumferential periphery that exhibits either an external or internal thread for operative engagement to each other. In FIG. 7, the front hub 31 includes an externally threaded extension 71, extending beyond the front hub cup (adapted to fit around the shaft of an introducer sheath (IS)), the extension accommodating the continuation of the longitudinal opening 36 to accommodate side loading of the shaft of introducer sheath (IS). Similarly rear hub 32 includes internally threaded extension 72 that extends beyond the cavity 40 of rear hub 32 in sufficient length to engage the externally threaded extension 71 of the front hub when the compression device assembly is placed around the shaft and proximal portion of an introducer sheath (IS). As with the front hub in this embodiment, the rear hub extension 72, accommodates the continuation of the longitudinal opening 37 to accommodate side loading of the proximal hemostasis portion (H) of introducer sheath (IS).

In operation, compression plug 42 is placed within the cavity of the rear hub, and the shaft and proximal end of the introducer sheath (IS) is side loaded into the lumen of the compression device 70. The operator then slidably engages the extension 71 of the front hub and extension 72 of the rear hub until they are in fixed engagement due to the mating of the opposite threads located thereon. The rear hub 32 can be threaded rotationally with the front hub (e.g. screwed on), or can be simply pushed straight on so that the threads engage like a ratchet mechanism. To release, manual pressure can be applied to the sidewall of the front hub extension 71 to disengage the threads thereon from the thread of the rear hub extension 72, or the rear hub can be rotationally removed by unscrewing it from the front hub.

Figure 8:
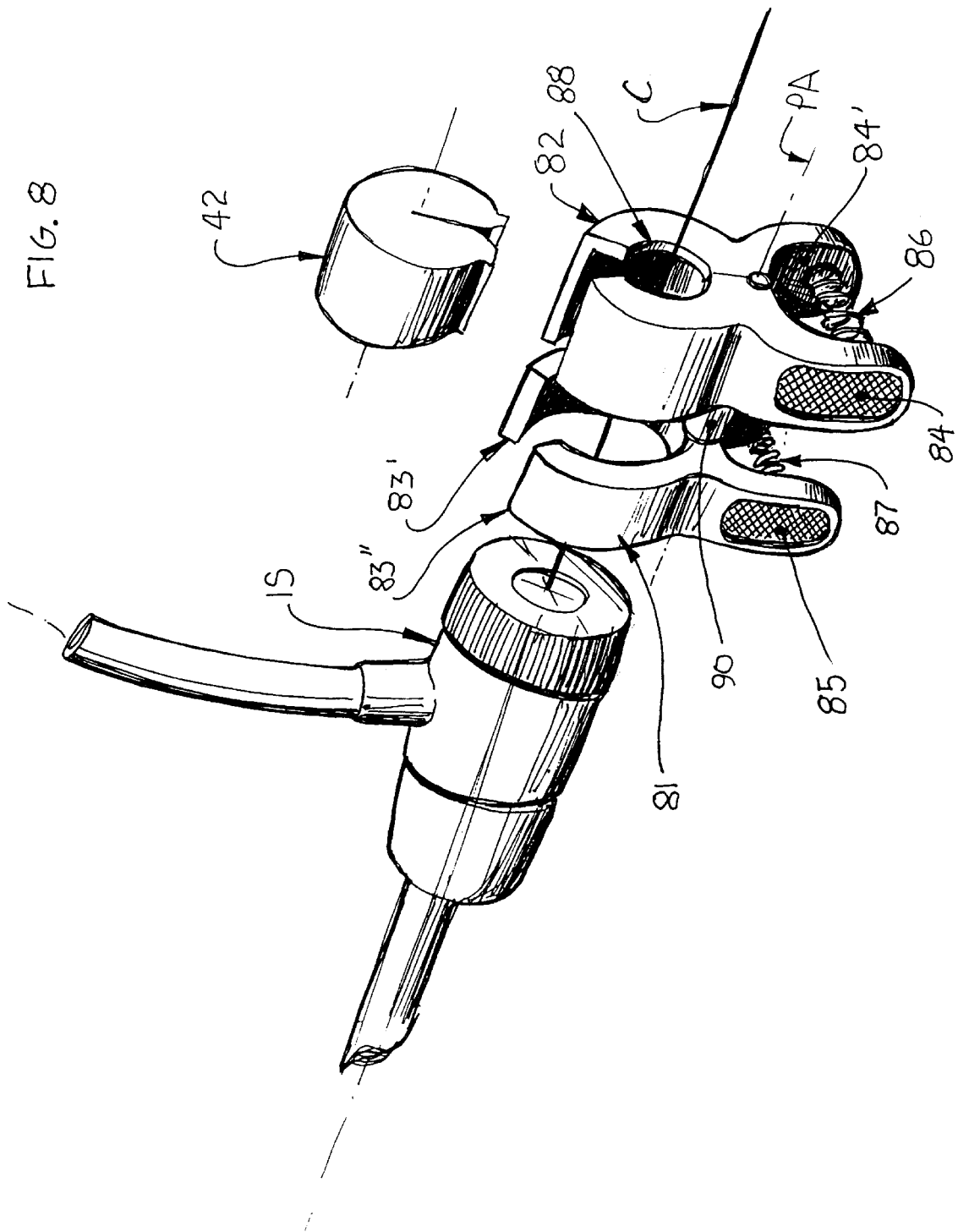
FIG. 8 illustrates still a further alternative embodiment of the present invention having a first and second clamp member pivotally attached to each other for purposes of placing said clamp members around the circumference of a standard introducer sheath proximal end. Said rear clamp member includes a housing to receive a compression plug of the present invention.

In still a further embodiment of the present invention as illustrated by FIG. 8, the compression device 80 has a first and second clamp member 81 and 82 respectively, pivotally engaged for placement over an introducer sheath (IS) for purposes of applying circumferential and axial pressure against the leaky portion of the sheath. Front clamp body 81 has a first and second jaw portion 83' and 83" formed in a circumferential configuration for receipt of the sheath (IS) shaft. The first and second jaw portions 83' and 83" include finger tab portions 85 and 85' extending bilaterally below the front clamp body. Finger tab portion 85 and 85' are operatively connected by a spring member 87, adapted to be placed in tension between finger tab portions 85 and 85' to apply circumferential pressure against the sheath portion inserted in the front clamp body 81. Front hub 81 can be released by applying manual pressure to pinch finger tab portions 85 and 85' toward one another.

Rear clamp body 82 has a first and second jaw portions 84 and 84', formed in a substantially circumferential configuration to accommodate both a compression plug 42 against the proximal end thereof, and the proximal sheath hemostasis portion (H) more distally. As with the front clamp body, rear clamp body 82 includes a finger tab portion 84 and 84, extending bilaterally below the rear clamp body. Finger tab portion 84 and 84' are operatively connected by a spring member 86, adapted to be placed in tension between finger tab portions 84 and 84' to apply circumferential pressure against the proximal sheath portion inserted in the rear clamp body 82. In addition to the circumferential pressure exerted thereon, the rear hub portion is adapted to include a flange portion 88, against which the compression plug 42 rests when positioned in the clamp cavity, to urge the compression plug 42 axially against the rear portion of the introducer sheath (IS) thereby applying direct pressure to any hemostasis device located therebetween. Rear hub 82 can be release by applying manual pressure to pinch finger tab portions 84 and 84' toward one another.

Front clamp portion 81 and rear clamp portion 82 are pivotally connected by a central pivot rod 90 to which the apex of each bilateral finger tab portion is attached. The front and rear clamp portion of this embodiment can be operated independently of each other depending on the preference of the operator, however, each clamp operates around the same pivot axis (PA) to assist in optimal hemostasis.

Figure 9:
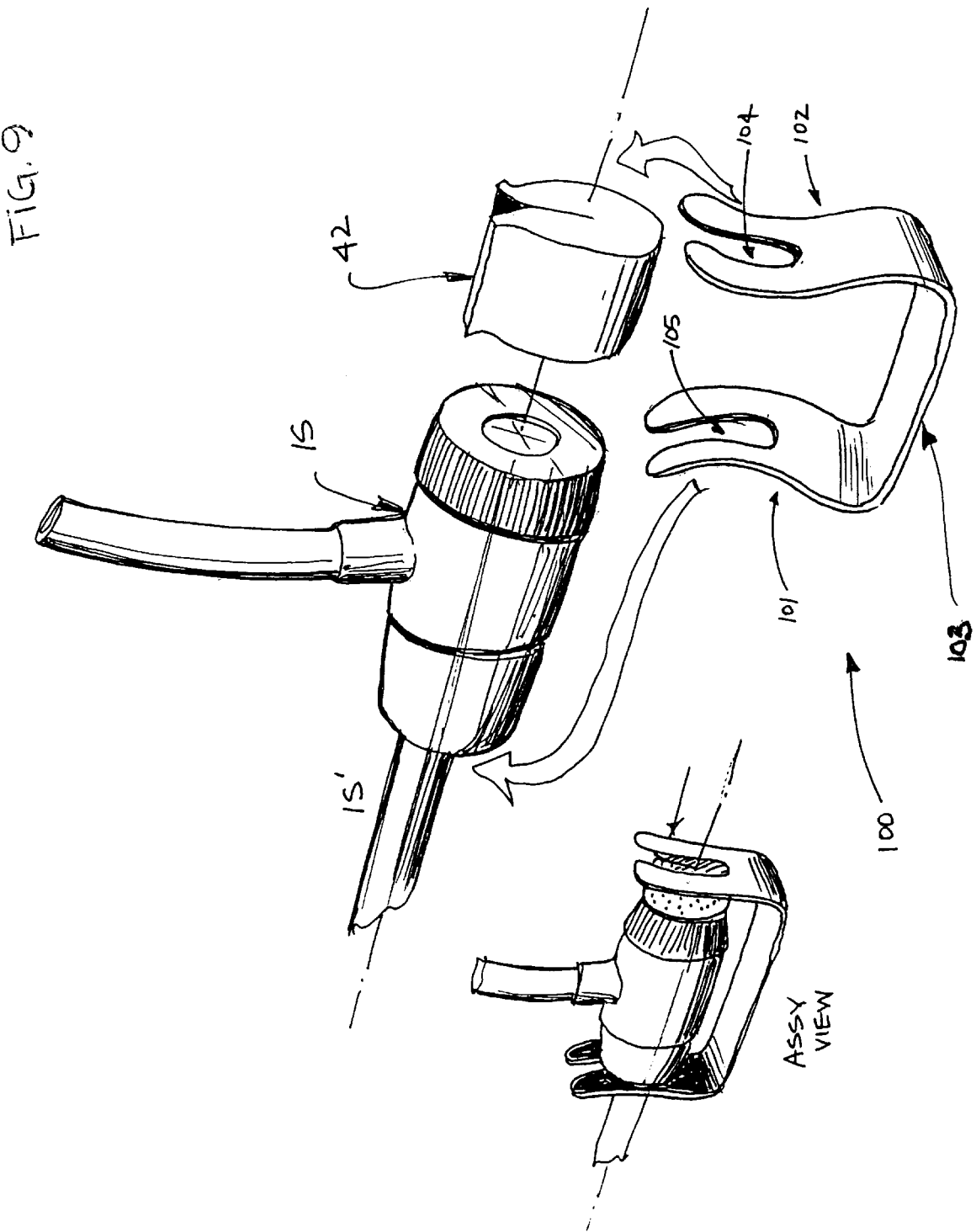
FIG. 9 illustrates an embodiment of the present invention wherein the body of the sealing device of the present invention is an integral unit.

FIG. 9 illustrates a schematic of the device of the present invention wherein the body of the device is constructed in an integral configuration, either as a one piece device, or separate elements secured together. The body portion 100 has a front hub portion 101 extending laterally from the main body portion 103 with a slot 105 located therein for receipt of the instrument (IS') shaft and a rear hub portion 102 extending laterally from the main body portion 103 at some distance away from the front hub portion, and also including a slot 104 to allow instruments to still be passed through the indwelling instrument following application of the device of the present invention. In the case of the device that is constructed in one piece the main body and front and rear hubs may be formed of a resilient material, the front and rear hub portions being biased toward each other in the relaxed configuration and put in tension to install the device around an instrument. In the case of the device that is integrally formed from multiple elements, the main body portion may be a resilient element such as a longitudinal spring or multiple springs that in the relaxed position force the front and rear hub together.

In operation, the tension would be momentarily applied to the main body portion by pulling the front and rear hubs in opposite directions (to allow placement of the front and rear hubs around the shaft and proximal end of an introducer sheath) and releasing said tension to allow the front and rear hub to resiliently compress, thereby exerting a sealing force against each other and any devices or material trapped therebetween. The assembly view of FIG. 9 shows the application of the integral device of this embodiment, including compression plug 42 inserted between the rear hub portion 102 and the proximal part of the leaking instrument.

Figure 10:
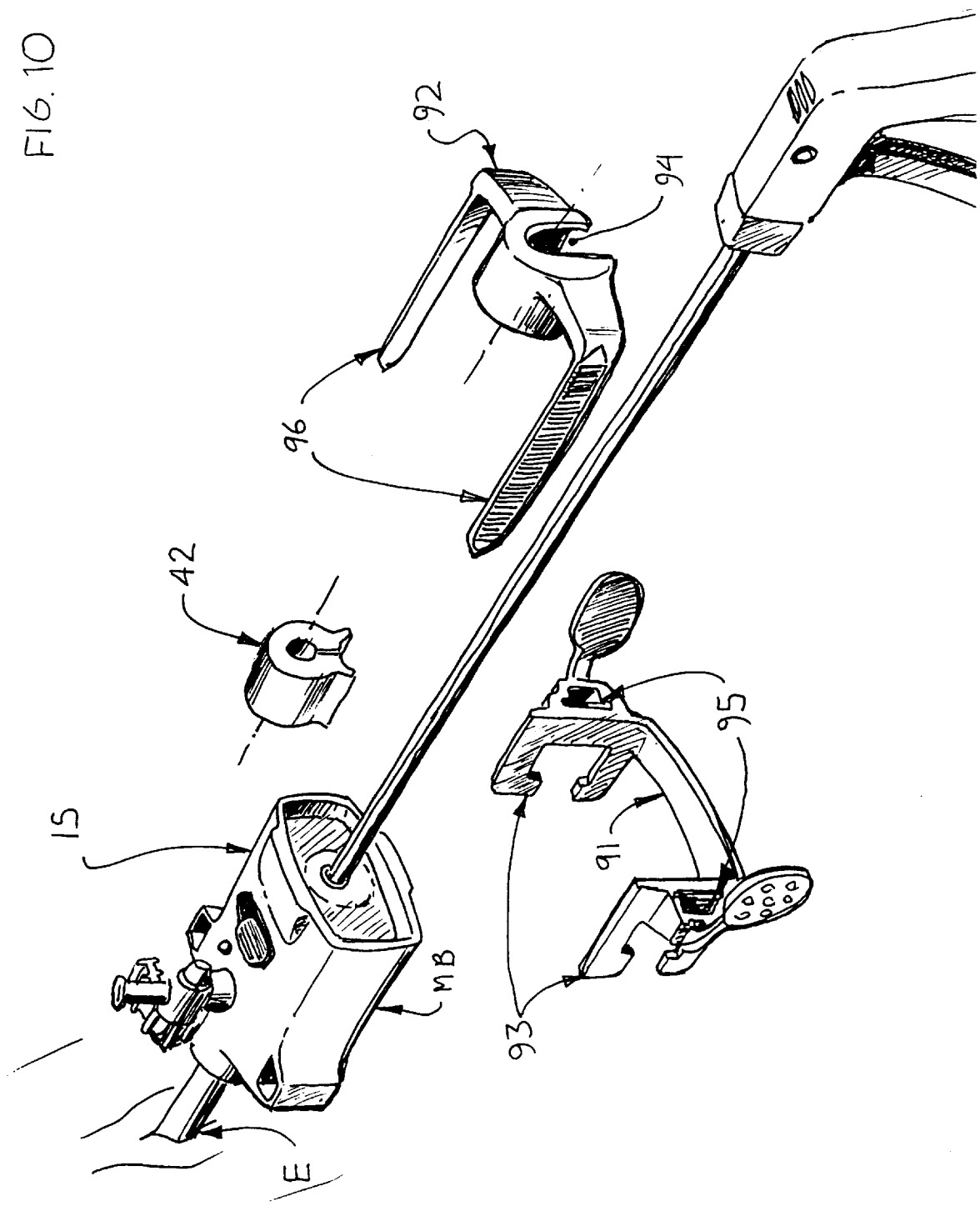
FIG. 10 illustrates the present invention as applied to the main body of a laparoscopic trocar device to seal the trocar port while still allowing the placement of laparoscopic instruments therethrough.

In still a further embodiment, FIG. 10 illustrates the use of the present invention for sealing $CO_2$ gas leaks at the port of a laparoscopic trocar device. The front hub 91 is provided with flexible clamping fixtures 93 adapted to clamp onto the main body of the laparoscopic device (MB). As described in the earlier embodiments, front hub side slots 95 and release levers 97 located on either side of the front hub body 91, for connecting with the rear hub 92. Similar to the description in earlier embodiments, rear hub 92 is formed in a hemispherical configuration with an inner and outer periphery. The inner periphery of rear hub 92 forms a cavity 94 for housing the compression plug 42. The outer periphery of rear hub 92 includes projections 96 that extend laterally from rear hub 92 and then longitudinally along the axis of the center lumen of rear hub 92. In operation front hub 91 would be secured to the main body of the trocar device (MB), and rear hub 92, housing compression device 42, would be advanced such that the projections 96 are slidably received by slots 95 of front hub 91 until the desired hemostasis is achieved.

The typical diameter of a laparoscopic trocar device ranges in the dimensions of 1.0" to 2.0".

While the above is a complete description of the preferred embodiments of the invention, various alternatives, modifications, and equivalents may be used. Therefore, the above description should not be taken as limiting the scope of the present invention, which rather are defined by the accompanying claims.

We claim:

1. A sealing device for minimizing gas or fluid leakage from a sheath device when said sheath device is inserted into a patient, wherein said sheath device has a shaft configured to receive a therapeutic or diagnostic device therethrough, said shaft defining a longitudinal axis of said sheath device and terminating at a proximal end of said sheath device, said sealing device comprising:

a compressible, resilient plug adapted for positioning at said proximal end of said sheath device, said plug having a longitudinal axis and a slit extending from said axis to an outer surface of said plug to receive said therapeutic or diagnostic device; and means for compressing said plug adapted to receive said therapeutic or diagnostic device and to exert axial pressure against said proximal end of said sheath device and inward radial pressure against said therapeutic or diagnostic device when received through said sheath device.

2. The sealing device of claim 1 wherein said compressible, resilient plug is formed of silicone.

3. A sealing device for minimizing gas or fluid leakage from a sheath device when said sheath device is inserted into a patient, wherein said sheath device has a shaft configured to receive a therapeutic or diagnostic device therethrough, said shaft defining a longitudinal axis of said sheath device and terminating at a proximal end of said sheath device, said sealing device comprising:

a compressible, resilient plug adapted for positioning at said proximal end of said sheath device, said plug having a longitudinal axis and a slit extending from said axis to an outer surface of said plug to receive said therapeutic or diagnostic device;

a front hub portion having a first engaging means and a rear hub portion having a second engaging means, said one or other of said first or second hub portions configured to receive said plug and said therapeutic or diagnostic device therein, such that when said first hub portion and said second hub portion are placed about the longitudinal axis of said sheath device and are moved toward one another, said first engaging means slidably mates with said second engaging means thereby causing said plug to compress and exert axial pressure against said proximal end of said sheath device and and inward radial pressure against said therapeutic or diagnostic device when received through said sheath device.

4. The sealing device of claim 3 wherein said compressible, resilient plug is formed of silicone.

5. A sealing device for minimizing gas or fluid leakage from a sheath device when said sheath device is inserted into a patient, wherein said sheath device has a shaft configured to receive a therapeutic or diagnostic device therethrough, said shaft defining a longitudinal axis of said sheath device and terminating at a proximal end of said sheath device, said sealing device comprising:

a compressible, resilient plug adapted for positioning at said proximal end of said sheath device, said plug having a longitudinal axis and a slit extending from said axis to an outer surface of said plug to receive said therapeutic or diagnostic device;

a first hub portion having a first outer periphery located therearound and a receiving slot located along said first outer periphery, a second hub portion having a second outer periphery located therearound and a projection element located along said second outer periphery, said second hub portion further defining a cavity bordered by said second outer periphery and configured to receive said plug and said therapeutic or diagnostic device therein such that when said first hub portion and said second hub portion are placed on either side of said proximal end of said sheath device, said projection element of said second hub portion is interconnected with said receiving slot of said first hub portion, thereby causing said plug to compress and exert axial pressure against said proximal end of said sheath device and and inward radial pressure against said therapeutic or diagnostic device when received through said sheath device.

6. The sealing device of claim 5 wherein said compressible, resilient plug is formed of silicone.

7. A sealing device for minimizing gas or fluid leakage from a sheath device when said sheath device is inserted into a patient, wherein said sheath device has a shaft configured to receive a therapeutic or diagnostic device therethrough, said shaft defining a longitudinal axis of said sheath device and terminating at a proximal end of said sheath device, said sealing device comprising:
  a compressible, resilient plug adapted for positioning at said proximal end of said sheath device, said plug having a longitudinal axis and a slit extending from said axis to an outer surface of said plug to receive said therapeutic or diagnostic device;
  front and rear hub portions, said hub portions having reciprocal external or internal threads for mating engagement and said one or other of said first or second hub portions configured to receive said plug and said therapeutic or diagnostic device therein, such that when said first hub portion and said second hub portion are placed about the longitudinal axis of said sheath device and are moved toward one another, the corresponding threads of each hub portion are engaged, thereby causing said plug to compress and exert axial pressure against said proximal end of said sheath device and and inward radial pressure against said therapeutic or diagnostic device when received through said sheath device.

8. The sealing device of claim 7 wherein said compressible, resilient plug is formed of silicone.

9. A sealing device for minimizing gas or fluid leakage from a sheath device when said sheath device is inserted into a patient, wherein said sheath device has a shaft configured to receive a therapeutic or diagnostic device therethrough, said shaft defining a longitudinal axis of said sheath device and terminating at a proximal end of said sheath device, said sealing device comprising:
  a compressible, resilient plug adapted for positioning at said proximal end of said sheath device, said plug having a longitudinal axis and a slit extending from said axis to an outer surface of said plug to receive said therapeutic or diagnostic device; and
  biasing means for compressing said plug adapted to receive said therapeutic or diagnostic device and to exert axial pressure against said proximal end of said sheath device and inward radial pressure against said therapeutic or diagnostic device when received through said sheath device.

10. The sealing device of claim 9 wherein said compressible, resilient plug is formed of silicone.

11. An introducer sheath assembly comprising:
  a shaft portion terminating at a proximal end of said sheath, said shaft portion defining a longitudinal axis of said sheath assembly and being configured to receive a therapeutic or diagnostic device therethrough;
  a front hub portion integral to said proximal end of said sheath assembly, said hub portion having a first engaging means;
  a compressible, resilient plug adapted for positioning at said proximal end of said sheath, said plug having a longitudinal axis and a slit extending from said axis to an outer surface of said plug to receive said therapeutic or diagnostic device; and
  a rear hub portion configured to receive said plug and said therapeutic or diagnostic device therein, said rear hub portion having a second engaging means, said second engaging means configured for reciprocal engagement with said first engaging means;
  wherein when said first hub portion and said second hub portion are moved toward one another, said first and second engaging means engage thereby causing said plug to compress and exert axial pressure against said proximal end of said sheath and inward radial pressure against said therapeutic or diagnostic device when received through said sheath.

12. The sealing device of claim 11 wherein said compressible, resilient plug is formed of silicone.

13. An laproscopic trocar assembly comprising:
  a trocar device having a main body and a port for receiving a laproscopic instrument therethrough;
  a front hub portion secured to said main body, said hub portion having a first engaging means;
  a compressible, resilient plug adapted for positioning at said port, said plug having a longitudinal axis and a slit extending from said axis to an outer surface of said plug to receive said laproscopic instrument; and
  a rear hub portion configured to receive said plug and said laproscopic instrument therein, said rear hub portion having a second engaging means, said second engaging means configured for reciprocal engagement with said first engaging means of said front hub portion;
  wherein when said first hub portion and said second hub portion are moved toward one another, said first and second engaging means engage thereby causing said plug to compress and exert axial pressure against said proximal end of said sheath and inward radial pressure against said laproscopic instrument when received through said port.

14. The sealing device of claim 13 wherein said compressible, resilient plug is formed of silicone.

15. A method of maintaining hemostasis at an introducer sheath proximal end, said introducer sheath having a therapeutic or diagnostic device introduced therethrough, said method comprising the steps of:
  providing a sealing device having
    a compressible, resilient plug adapted for positioning at said proximal end of said sheath device, said plug having a longitudinal axis and a slit extending from said axis to an outer surface of said plug to receive said therapeutic or diagnostic device, and
    first and second hub portions having reciprocal first and second engaging means, respectively, said one or other of said first or second hub portions configured to retain said plug and said therapeutic or diagnostic device therein;
  placing said first hub portion and said second hub portion on either side of said introducer sheath such that said introducer sheath proximal end is located therebetween and said therapeutic or diagnostic device is received in said plug slit;

moving said first hub portion and said second hub portion toward one another such that the first and second hub portions cause said plug compress and apply axial pressure to the introducer sheath proximal end and inward radial pressure to the diagnostic or therapeutic device, thereby reducing any leakage or fluid therefrom.

16. The method of claim 15 wherein said moving step further comprises engaging said first and second engaging means of said first and second hub portions, thereby maintaining said plug in a compressed state.

* * * * *